United States Patent [19]

Cary

[11] Patent Number: 5,397,765
[45] Date of Patent: Mar. 14, 1995

[54] METHOD AND COMPOSITIONS FOR PROTECTING MAIZE AGAINST INJURY FROM THE INTERACTION OF AN ORGANOPHOSPHATE INSECTICIDE-NEMATICIDE AND AN AHAS-INHIBITING HERBICIDE USING LACTIDICHLOR

[75] Inventor: Gail E. Cary, Lawrenceville, N.J.

[73] Assignee: American Cyanamid Company, Wayne, N.J.

[21] Appl. No.: 7,310

[22] Filed: Jan. 21, 1993

Related U.S. Application Data

[63] Continuation of Ser. No. 733,511, Jul. 22, 1991, abandoned.

[51] Int. Cl.$^6$ .................. A01N 25/32; A01N 37/10; A01N 43/40; A01N 43/50
[52] U.S. Cl. ............................ 504/110; 504/103
[58] Field of Search ............................ 504/110

[56] References Cited

U.S. PATENT DOCUMENTS

| | | | |
|---|---|---|---|
| 3,564,768 | 2/1971 | Hoffman | 71/190 |
| 4,137,070 | 1/1979 | Pallos et al. | 71/100 |
| 4,388,473 | 6/1983 | Richter et al. | 560/65 |
| 4,789,397 | 12/1988 | Taylor | 71/107 |
| 4,936,901 | 6/1990 | Surgant, Sr. et al. | 71/92 |
| 5,129,949 | 7/1992 | Cary | 504/110 |

FOREIGN PATENT DOCUMENTS

WO92/11761 7/1992 WIPO .

OTHER PUBLICATIONS

Ogawa, Chemical Abstracts, vol. 111 (1989) 148896c.
*Progressive Farmer*. "A Chemical Reaction That Could Zap Corn" p. 68. Mar. 1990.

Primary Examiner—Glennon H. Hollrah
Assistant Examiner—S. Mark Clardy
Attorney, Agent, or Firm—John W. Hogan

[57] ABSTRACT

There is provided a method for inhibiting or preventing injury to a corn plant caused by the synergistic interaction of an organophosphate compound employed for the protection of the plant against attack by insects and nematodes and the use of an acetohydroxyacid synthase-inhibiting compound employed for the control of undesirable weed species in the locus of the plant comprising the application of an effective amount of naphthalic anhydride, the dipotassium salt of naphthalic acid, dicamba, 2,4-D, dichlormid, butyl 2-[(5-chloro-8-quinolyl)oxy]acetimidate, butyl [(5-chloro-8-quinolyl)oxy]acetate, 1-methylhexyl 2-[(5-chloro-8-quinolyl)oxy]acetate or 1-carbethoxyethyl-3,6-dichloro-2-methoxybenzoate. There is also provided a safened insecticidal composition.

8 Claims, No Drawings

METHOD AND COMPOSITIONS FOR PROTECTING MAIZE AGAINST INJURY FROM THE INTERACTION OF AN ORGANOPHOSPHATE INSECTICIDE-NEMATICIDE AND AN AHAS-INHIBITING HERBICIDE USING LACTIDICHLOR

This is a continuation of application Ser. No. 07/733,511, filed on Jul. 22, 1991, abandoned.

BACKGROUND OF THE INVENTION

This invention relates to methods and compositions for eliminating or preventing injury to a corn plant caused by the interaction of two or more pesticides applied to the plant in combination, either simultaneously or sequentially. Of particular concern are synergistic responses which occur on a single plant species. Synergistic responses obtained with combinations of herbicides, insecticides and fungicides are described as the combined action of two components of a mixture such that the total effect is greater or more prolonged than the sum of the effects of the two components taken independently.

More particularly, the invention provides methods and compositions for eliminating or preventing injury to a crop plant resulting from the interaction of an organophosphate pesticide and an acetohydroxyacid synthase-inhibiting herbicide. More particularly, this invention relates to methods of and compositions for preventing, inhibiting or ameliorating injury to plants resulting from the interaction of O,O-diethyl S-[(ethylthio)methyl]phosphorodithioate (phorate) or O,O-diethyl S-{[(1,1-dimethylethyl)thio]-methyl}phosphorodithioate (terbufos) and a sulfonylurea herbicide such as nicosulfuron or primisulfuron or an imidazolinone herbicide such as imazethapyr, imazamethapyr or imazaquin.

The ever increasing demands for greater quantities and improved quality of food to feed the expanding human population around the world has driven plant science agriculturalists to maximize crop yield and product quality for every hectare of land under cultivation. To this end, knowledgeable farm practitioners have found it advantageous to protect their crops from the time of planting through harvest and beyond against attack, infestation or encroachment by all types of pests including: insects, acarina, bacteria, fungi, nematodes and undesirable plant species. Thus, to achieve the desired protection it has become a rather common practice in the farming industry to use a multiplicity of pest control agents, applied either simultaneously or sequentially, to provide concurrent and continuous protection for the treated crop plant.

In many instances, it has been found that combination treatments afford plant protection against a variety of pests with a single application of combined pesticides or with simultaneous or sequential applications of two or more pesticides applied to the planted and/or growing crop. In practice, there are many known instances of considerable modifications in the biological activity of one pesticide brought about by the prior, simultaneous or sequential application of another pesticide to the same target species. When this occurs it is commonly referred to as an "interaction". As a result of pesticide interactions, adverse effects can occur; and the responses of target species such as corn plants to the combined applications of two or more pesticides are not predictable from the effect of each pesticide applied alone. Said interactions are described as antagonistic when the net effect is a decrease in the biological activity and synergistic when the net effect is an enhancement of biological activity. In other words, a synergistic interaction of a pesticide combination is a more than additive toxic action of two or more pesticides when used together. Pesticide combination applications which result in a synergistic interaction are herein described as synergistic pesticide combinations.

For the past two decades, terbufos and phorate have been used for the control of soilborne pests and as systemic insecticides. These compounds have been used successfully for the control of soilborne and leaf-feeding pests and have been utilized in conjunction with a variety of other pesticides without reports of undesirable interactions. Thus, it is surprising to find that with the recent introduction of certain AHAS inhibiting herbicides (for instance, sulfonylureas such as nicosulfuron and primisulfuron) there appears to be a synergistic interaction observed in corn plants which have been treated at planting with a soil insecticide such as disulfoton, chlorpyrifos, fonofos, phorate or terbufos and thereafter treated early postemergence or when the plants are in the seedling stage, i.e. about the three to five leaf stage, with nicosulfuron or primisulfuron.

It is believed that the synergistic interaction of certain organophosphate compounds with nicosulfuron or primisulfuron occurs when an organophosphate compound is taken into the root system of a plant and inhibits the plant's ability to metabolize the sulfonylurea compound. This inhibition permits the sulfonylurea compound to accumulate in the plant tissue and reach levels which can cause significant injury to the plant.

It is, therefore, an object of this invention to provide methods and compositions for inhibiting, preventing or ameliorating injury to a corn plant resulting from the synergistic interaction of two or more chemicals applied to said plant or the locus in which it is planted or growing.

A further object of this invention is to provide methods and compositions for protecting a corn plant from attack by soilborne pests and preventing incursion into the corn growing area of undesirable plant species while inhibiting or preventing injury to the corn plant due to the synergistic interaction between an organophosphate insecticide and an AHAS-inhibiting herbicide.

DESCRIPTION OF THE INVENTION

Surprisingly it has been found that the pesticide interaction of an organophosphate insecticide and an AHAS-inhibiting herbicide can be safened by the addition of a third chemical. The third chemical is herein referred to as a safener compound. The present invention includes a method of protecting corn plants from injury resulting from the synergistic interaction of a systemic organophosphate insecticide such as terbufos or phorate and an AHAS-inhibiting herbicide such as nicosulfuron or primisulfuron by applying an effective amount of a safener compound selected from the group consisting of 1,8-napthalic anhydride, the dipotassium salt of napthalic acid (herein referred to as NAK), 3,6-dichloro-2-methoxybenzoic acid (dicamba), 2,4-dichlorophenoxy acetic acid (2,4-D), dichloroacetamide compounds such as N,N-diallyl-2,2-dichloroacetamide (dichlormid), hydroxyquinoline compounds such as butyl 2-[(5-chloro-8-quinolyl)oxy] acetimidate and 1-carbethoxyethyl 3,6-dichloro-2-methoxybenzoate.

The organophosphate insecticide of the invention includes terbufos, phorate, fonofos, disulfoton, chlorpyrifos and the like, preferably terbufos or phorate. The AHAS-inhibiting herbicide includes a sulfonyl urea herbicide, preferably nicosulfuron or primisulfuron and an imidazolinone herbicide, preferably imazethapyr, imazamethapyr or imazaquin.

The safener compounds of the present invention have a variety of uses but previously have not been used for safening maize from injury caused by a synergistic pesticide interaction. Suitable safener compounds of the invention include: 1-carbethoxyethyl 3,6-dichloro-2-methoxybenzoate, 1,8-naphthalic anhydride, NAK, dicamba and 2,4-D. Further suitable safener compounds include dichloroacetamide compounds and hydroxyquinoline compounds. Dichloroacetamide compounds include 4-(dichloroacetyl)-3,4-dihydro-3-methyl-2H-1,4-benzoxazine, 1-dichloroacetyl-hexahydro-3,3-8α-trimethyl-pyrrolo-[1,2-α]pyrimidin-6-(2H)-one, 2-dichloromethyl-2-methyl-1,3-dioxolane, N-dichloroacetyl-1-oxa-4-aza-spiro-4,5-decane, dichlormid and the like. Hydroxyquinoline compounds include butyl 2-[(5-chloro-8-quinolyl)oxy]acetimidate, butyl [(5-chloro-8-quinolyl)oxy]acetate, 1-methylhexyl[(5-chloro-8-quinolyl)oxy]acetate and the like.

The safener compound can be applied in a variety of ways. For instance, the safener compound can be applied (1) to the soil, (2) to the crop plant seed, (3) to the crop plant or (4) in combination with the insecticide. If the safener compound is applied to the soil, it can be applied before, in conjunction with or after the insecticide. The safener may be applied to the soil in-furrow, preplant incorporated or preemergence.

In another embodiment of the present invention, the safener compound may be applied to the corn plant seed. Conventional seed treatment techniques using the safener compounds of the present invention may be employed to give satisfactory safening of the pesticide interaction.

If the safener compound is applied postemergence to the corn plants, generally it may be applied as a foliar spray. This application technique may be employed prior to herbicidal treatment or at the same time as herbicidal treatment. While it is contemplated that the safener compound may be applied a short time after application of herbicide, it is generally less effective, since some injury from the synergistic pesticide interaction may result. For convenience, when applying the safener compound postemergence, it is best to apply it simultaneously with the herbicide such as in a tank mix.

Further, the safener compound may be applied in combination with the organophosphate insecticide. For example, the formulated insecticide may be coated with the safener compound. It is also contemplated that the safener compounds may be premixed with the technical insecticide such as terbufos or phorate prior to the final formulation. For example, the premixed soil insecticide-nematicide and safener compound may be applied directly to a suitable carrier such as clay, attapulgite, BIODAC®, montmorillonite and the like, or may be homogeneously mixed with a plastic formulation such as a polyvinyl chloride or a starch-like formulation.

Compositions are provided in which an effective amount of the safener compound is intimately dispersed in an inert carrier or liquid diluent. An inert carrier is one that will not react with the safener compound and is suitable for agronomic use.

Typical compositions of the invention include wettable powders, dusts, granules, sprays and the like. The inventive compositions are suitable for application to the soil, to the formulated insecticide or to the corn seed either directly or after an intermediate dilution or blending step.

In order to facilitate a further understanding of the invention, the following examples are presented primarily for the purpose of illustrating certain more specific details thereof. The invention is not to be deemed limited thereby except as defined in the claims.

EXAMPLE 1

Evaluation of 1,8-naphthalic anhydride as a seed treatment on the synergistic interaction between two pesticides Corn seeds (Pioneer 3475) are coated with naphthalic anhydride (ADVANTAGE, manufactured by FMC corporation, 91% active ingredient). Seeds are coated with naphthalic anhydride at rates ranging from 0.05 grams per 100 grams seed (equal to 0.05% by seed weight), to 0.5 grams per 100 grams seed (equal to 0.5% by seed weight).

Experiments are conducted in sterilized loamy sand soil containing 5% organic matter. Soil is placed in 10-inch×10-inch×2-inch shallow plastic flats, and thoroughly moistened. Two six-inch furrows are made in each flat, into each furrow is placed five corn seeds, either coated or uncoated with the safener. The organophosphate insecticide terbufos manufactured by American Cyanamid Company is applied to one furrow as the 15% granular formulation (COUNTER® 15G) at a rate equivalent to 1.0 kg/ha of active ingredient; the other furrow is left untreated.

Plants are sprayed postemergence with a herbicide at about the 2–4 leaf (5–8 inch) stage of growth. A commercial formulation of primisulfuron which contains 75% of active ingredient (BEACON® 75 DF, manufactured by Ciba-Geigy Co), is diluted with water to provide the equivalent of 0.04 kg/ha of active ingredient to the foliage when applied through a spray nozzle operating at 40 psi for a predetermined time. The herbicide spray solution contains 0.25% of the spray adjuvant CHARGER E, an alkylaryl polyethoxyethanol and N-butanol 80% non-ionic wetting agent manufactured by Blue Ribbon Products Co.

After spraying, flats are then placed on greenhouse benches, watered and cared for in accordance with conventional greenhouse procedures. From 2–4 weeks after treatment, the tests are terminated and each flat is examined and rated by measuring the height of the foliage. The test results are averaged and expressed as a percent growth reduction compared to an untreated check, using the following formula:

$$\% \text{ Growth Reduction} = 100 - \left[ \frac{\text{Height of Treated Plants}}{\text{Height of Untreated Plants}} \times 100 \right]$$

The data are shown in Table I.

TABLE I

| Treatment | Rate (kg/ha) | % Growth Reduction |
|---|---|---|
| Untreated check | 0.00 | 0 |
| Terbufos | 1.00 | 2 |
| Primisulfuron | 0.04 | 0* |
| Terbufos × Primisulfuron | 1.0 × 0.04 | 68 |
| Terbufos × Primisulfuron + naphthalic anhydride | 1.0 × 0.04 0.05% seed wt | 3 |
| Terbufos × Primisulfuron + naphthalic anhydride | 1.0 × 0.04 0.10% seed wt | 10 |
| Terbufos × Primisulfuron + naphthalic anhydride | 1.0 × 0.04 0.25% seed wt | 8 |
| Terbufos × Primisulfuron + naphthalic anhydride | 1.0 × 0.04 0.50% seed wt | 9 |

Shoot height of the untreated check was 82.6 cm
*Growth was 2% greater than the untreated check

EXAMPLE 2

Evaluation of 1,8-naphthalic anhydride applied directly to the insecticide on the synergistic interaction between two pesticides A mixture of naphthalic anhydride and a wettable powder formulation containing 5% Marasperse CBO, a sodium lignin sulfonate manufactured by Reed-Lignin, 1% Igepon T-77, an N-methyl-N-oleoyltaurate manufactured by GAF Industries, and 94% Attaclay, attapulgite fines manufactured by Englehardt is prepared to provide a formulation containing 20% active ingredient. This mixture is applied to terbufos, formulated as 15% active ingredient on Creek-o-Nite clay granules (COUNTER ® 15G), by shaking thoroughly. Amounts of the wettable powder equal to 6, 12, 24 and 50 milligrams, are applied to 0.125 grams of COUNTER ® 15G to provide in-furrow rates equivalent to 1.0 kg/ha terbufos and 0.063–0.5 kg/ha naphthalic anhydride.

Experiments are conducted in either a plano silt loam soil or a loamy sand soil containing 5% organic matter. Soil is placed in 10-inch × 10-inch × 2-inch shallow plastic flats, and thoroughly moistened. Two six-inch furrows are made in each flat, five corn seeds are placed in each furrow. Terbufos is applied to one furrow either as the untreated 15% granular formulation (COUNTER ® 15G), or the treated granular formulation containing naphthalic anhydride.

The furrows are closed and the plants are allowed to grow to about the 2–4 leaf stage at which time the plants are sprayed postemergence with the herbicide primisulfuron as described in Example 1.

After 2–4 weeks of greenhouse care, the tests are terminated and the plants evaluated as described in Example 1.

The results are shown in Table II.

TABLE II

| | | % Growth Reduction | |
|---|---|---|---|
| Treatment | Rate (kg/ha) | (A) Plano Silt Loam | (B) Loamy Sand |
| Untreated check | 0.00 | 0 | 0 |
| Terbufos | 1.00 | 11 | 6 |
| Primisulfuron | 0.04 | 9 | 12 |
| Terbufos × Primisulfuron | 1.0 × 0.04 | 57 | 33 |
| Terbufos × Primisulfuron + naphthalic anhydride | 1.0 × 0.04 0.063 | 34 | 18 |
| Terbufos × Primisulfuron + naphthalic anhydride | 1.0 × 0.04 0.125 | 34 | 20 |
| Terbufos × Primisulfuron + naphthalic anhydride | 1.0 × 0.04 0.25 | 19 | 10 |
| Terbufos × Primisulfuron + naphthalic anhydride | 1.0 × 0.04 0.50 | 17 | 14 |

(A) Shoot height of the untreated check was 41.6 cm
(B) Shoot height of the untreated check was 93.2 cm

EXAMPLE 3

Evaluation of a foliar application of the dipotassium salt of naphthalic acid (NAK) on the synergistic interaction between two pesticides Experiments are conducted in a loamy sand soil containing 5% organic matter. Soil is placed in 10-inch × 10-inch × 2-inch shallow plastic flats, and thoroughly moistened. Two six-inch furrows are made in each flat, into each furrow are placed five corn seeds. The organophosphate insecticide, terbufos, is applied to one furrow as the 15% granular formulation (COUNTER ® 15G) at a rate equivalent to 1 kg/ha; the other furrow is left untreated.

When plants have reached the 2–4 leaf stage, they are sprayed with an aqueous solution containing 0.25% CHARGER E surfactant, the dipotassium salt of naphthalic acid (NAK) and the sulfonylurea herbicide primisulfuron in sufficient quantities to provide 0–1.0 kg/ha of NAK and 0.04 kg/ha of primisulfuron when applied to the plants with a 40 psi nozzle. After spraying, plants are maintained in a greenhouse, and the test evaluated as described in Example 1.

The results are reported in Table III.

TABLE III

| Treatment | Rate (kg/ha) | % Growth Reduction |
|---|---|---|
| Untreated check | 0.00 | 0 |
| Terbufos | 1.00 | 3 |
| Primisulfuron | 0.04 | 13 |
| Terbufos × Primisulfuron | 1.0 × 0.04 | 41 |
| Terbufos × Primisulfuron + NAK | 1.0 × 0.04 0.50 | 15 |
| Terbufos × Primisulfuron + NAK | 1.0 × 0.04 0.75 | 13 |
| Terbufos × Primisulfuron + NAK | 1.0 × 0.04 1.00% | 16 |

Shoot height of the untreated check was 73.2 cm

EXAMPLE 4

Evaluation of dichlormid as a seed treatment on the synergistic interaction between two pesticides Corn seeds (Pioneer 3475) are treated with the safener dichlormid (2,2-dichloro-N-N-di-2-propenylacetamide) by first making a stock solution of the safener in 2.5 milliters of an acetone:dimethylformamide (10:1) mixture. Aliquots of the stock solution ranging from 62.5 microliters to 1.0 milliliter are added to 10 grams of corn seed and shaken thoroughly to provide safener seed treatment rates equivalent to 0.025%–0.4% by seed weight.

Treated and untreated seeds are planted in 6" furrows made in a loamy sand soil containing 5% organic matter. One-half of the furrows are treated with the insecticide terbufos, as described in Example 1.

The plants are grown to the 2–4 leaf stage and are treated postemergence with the herbicide primisulfuron as described in Example 1. After 2–4 weeks of greenhouse care the plants are evaluated as described in Example 1.

The results are shown in Table IV.

TABLE IV

| Treatment | Rate (kg/ha) | % Growth Reduction |
|---|---|---|
| Untreated check | 0.00 | 0 |
| Terbufos | 1.00 | 0* |
| Primisulfuron | 0.04 | 13 |
| Terbufos × Primisulfuron | 1.0 × 0.04 | 45 |
| Terbufos × Primisulfuron + Dichlormid | 1.0 × 0.04 0.025% seed wt | 14 |
| Terbufos × Primisulfuron + Dichlormid | 1.0 × 0.04 0.05% seed wt | 21 |
| Terbufos × Primisulfuron + Dichlormid | 1.0 × 0.04 0.10% seed wt | 22 |
| Terbufos × Primisulfuron + Dichlormid | 1.0 × 0.04 0.02% seed wt | 17 |
| Terbufos × Primisulfuron + Dichlormid | 1.0 × 0.04 0.4% seed wt | 24 |

Shoot height of the untreated check was 80.6 cm
*Growth was 6% greater than the untreated check

EXAMPLE 5

Evaluation of dichlormid applied directly to the soil on the synergistic interaction between two pesticides Experiments are conducted in a loamy sand soil containing 5% organic matter. Soil is placed in 10-inch×10-inch×2-inch shallow plastic flats, and thoroughly moistened. Two six-inch furrows are made in each flat, into each are placed five corn seeds. The organophosphate insecticide terbufos is applied to one furrow as the 15% granular formulation (COUNTER ® 15G) at a rate equivalent to 1.0 kg/ha; the other furrow is left untreated. The furrows are closed.

The safener dichlormid is applied to the soil surface by spraying with an 80% acetone solution containing dichlormid in sufficient quantities to provide a rate equivalent to 0–1.0 kg/ha when applied with a 40 psi nozzle. After spraying, the soil surface is covered with a thin layer of untreated soil.

When the plants have reached the 2–4 leaf stage, they are sprayed with the herbicide primisulfuron as described in Example 1.

The plants are given greenhouse care for 2–4 weeks and are evaluated as described in Example 1.

The results are shown in Table V.

TABLE V

| Treatment | Rate (kg/ha) | % Growth Reduction |
|---|---|---|
| Untreated check | 0.00 | 0 |
| Terbufos | 1.00 | 0* |
| Primisulfuron | 0.04 | 0** |
| Terbufos × Primisulfuron | 1.0 × 0.04 | 33 |
| Terbufos × Primisulfuron + Dichlormid | 1.0 × 0.04 0.032 | 28 |
| Terbufos × Primisulfuron + Dichlormid | 1.0 × 0.04 0.063 | 22 |
| Terbufos × Primisulfuron + Dichlormid | 1.0 × 0.04 0.125 | 11 |
| Terbufos × Primisulfuron + Dichlormid | 1.0 × 0.04 0.25 | 2 |
| Terbufos × Primisulfuron + Dichlormid | 1.0 × 0.04 0.50 | 1 |
| Terbufos × Primisulfuron + Dichlormid | 1.0 × 0.04 0.75 | 8 |
| Terbufos × Primisulfuron + Dichlormid | 1.0 × 0.04 1.00 | 8 |

Shoot height of the untreated check was 79.5 cm
*Growth was 16% greater than the untreated check
**Growth was 3% greater than the untreated check

EXAMPLE 6

Evaluation of a foliar application of dichlormid on the synergistic interaction between two pesticides The procedure used is as described in Example 3, except that plants are sprayed with an aqueous solution containing 0.25% CHARGER E surfactant, dichlormid, and the sulfonylurea herbicide primisulfuron in sufficient quantities to provide 0–1.0 kg/ha of dichlormid and 0.04 kg/ha of primisulfuron when applied to the plants with a 40 psi nozzle.

The results are shown in Table VI.

TABLE VI

| Treatment | Rate (kg/ha) | % Growth Reduction |
|---|---|---|
| Untreated check | 0.00 | 0 |
| Terbufos | 1.00 | 0* |
| Primisulfuron | 0.04 | 6 |
| Terbufos × Primisulfuron | 1.0 × 0.04 | 67 |
| Terbufos × Primisulfuron + Dichlormid | 1.0 × 0.04 0.063 | 59 |
| Terbufos × Primisulfuron + Dichlormid | 1.0 × 0.04 0.125 | 35 |
| Terbufos × Primisulfuron + Dichlormid | 1.0 × 0.04 0.025 | 31 |
| Terbufos × Primisulfuron + Dichlormid | 1.0 × 0.04 0.50 | 17 |
| Terbufos × Primisulfuron + Dichlormid | 1.0 × 0.04 0.75 | 18 |
| Terbufos × Primisulfuron + Dichlormid | 1.0 × 0.04 1.00 | 3 |

Shoot height of the untreated check was 80.6 cm
*Growth was 6% greater than the untreated check

EXAMPLE 7

Evaluation of 1-carbethoxyethyl 3,6-dichloro-2-methoxybenzoate as a seed treatment on the synergistic interaction between two pesticides The procedure used is as described in Example 4, except that seeds are treated with 1-carbethoxyethyl 3,6-dichloro-2-methoxybenzoate prior to planting.

The results are shown in Table VII.

TABLE VII

| Treatment | Rate (kg/ha) | % Growth Reduction |
|---|---|---|
| Untreated check | 0.00 | 0 |
| Terbufos | 1.00 | 0* |
| Primisulfuron | 0.04 | 0** |
| Terbufos × Primisulfuron | 1.0 × 0.04 | 38 |
| Terbufos × Primisulfuron + 3,6-dichloro-2-methoxy-benzoic acid, 1-carboxy-ethyl ester | 1.0 × 0.04 0.025% seed wt | 53 |
| Terbufos × Primisulfuron + 3,6-dichloro-2-methoxy-benzoic acid, 1-carboxy-ethyl ester | 1.0 × 0.04 0.05% seed wt | 29 |
| Terbufos × Primisulfuron + 3,6-dichloro-2-methoxy-benzoic acid, 1-carboxy-ethyl ester | 1.0 × 0.04 0.10% seed wt | 50 |
| Terbufos × Primisulfuron + 3,6-dichloro-2-methoxy-benzoic acid, 1-carboxy-ethyl ester | 1.0 × 0.04 0.2% seed wt | 22 |
| Terbufos × Primisulfuron + 3,6-dichloro-2-methoxy-benzoic acid, 1-carboxy-ethyl ester | 1.0 × 0.04 0.4% seed wt | 22 |

Shoot height of the untreated check was 68.0 cm
*Growth was 12% greater than the untreated check
**Growth was 2% greater than the untreated check

EXAMPLE 8

Evaluation of the foliar application of 1-carbethoxyethyl 3,6-dichloro-2-methoxybenzoate on the synergistic interaction between two pesticides The procedure used is the same as in Example 3, except that plants are sprayed with an aqueous solution containing 0.25% CHARGER E surfactant, 1-carbethoxyethyl 3,6-dichloro-2-methoxybenzoate and the sulfonylurea herbicide primisulfuron in sufficient quantities to provide 0–0.5 kg/ha of 1-carbethoxyethyl 3,6-dichloro-2-methoxybenzoate and 0.04 kg/ha of primisulfuron when applied to the plants with a 40 psi nozzle.

The results are shown in Table VIII.

TABLE VIII

| Treatment | Rate (kg/ha) | % Growth Reduction |
|---|---|---|
| Untreated check | 0.00 | 0 |
| Terbufos | 1.00 | 1 |
| Primisulfuron | 0.04 | 16 |
| Terbufos × Primisulfuron | 1.0 × 0.04 | 37 |
| Terbufos × Primisulfuron + 1-carbethoxyethyl 3,6-dichloro-2-methoxybenzoate | 1.0 × 0.04 0.063 | 35 |
| Terbufos × Primisulfuron + 1-carbethoxyethyl 3,6-dichloro-2-methoxybenzoate | 1.0 × 0.04 0.125 | 27 |
| Terbufos × Primisulfuron + 1-carbethoxyethyl 3,6-dichloro-2-methoxybenzoate | 1.0 × 0.04 0.25 | 18 |
| Terbufos × Primisulfuron + 1-carbethoxyethyl 3,6-dichloro-2-methoxybenzoate | 1.0 × 0.04 0.50 | 21 |

Shoot height of the untreated check was 79.0 cm

EXAMPLE 9

Evaluation of a foliar application of a hydroxyquinoline compound on the synergistic interaction between two pesticides The procedure used is the same as described in Example 3, except that plants are sprayed with a hydroxyquinoline compound, butyl 2-[(5-chloro-8-qinolyl)oxy]acetimidate (compound A) or butyl [5-chloro-8-qunolyl)oxy]acetate (compound B) and the sulfonylurea herbicide, primisulfuron in sufficient quantities to provide 0–1.0 kg/ha of a hydroxyquinoline compound and 0.04 kg/ha of primisulfuron when applied to the plants with a 40 psi nozzle.

The results are shown in Table IX.

TABLE IX

| Treatment | Rate (kg/ha) | % Growth Reduction |
|---|---|---|
| Untreated check | 0.00 | 0 |
| Terbufos | 1.00 | 3 |
| Primisulfuron | 0.04 | 13 |
| Terbufos × Primisulfuron | 1.0 × 0.04 | 41 |
| Terbufos × Primisulfuron + hydroxyquinoline Compound A* | 1.0 × 0.04 0.5 | 16 |
| Terbufos × Primisulfuron + hydroxyquinoline Compound A* | 1.0 × 0.04 0.75 | 24 |
| Terbufos × Primisulfuron + hydroxyquinoline Compound A* | 1.0 × 0.04 1.00 | 25 |
| Terbufos × Primisulfuron + hydroxyquinoline Compound B** | 1.0 × 0.04 0.5 | 22 |
| Terbufos × Primisulfuron + hydroxyquinoline Compound B** | 1.0 × 0.04 0.75 | 14 |
| Terbufos × Primisulfuron + hydroxyquinoline Compound B** | 1.0 × 0.04 1.00 | 17 |

Shoot height of the untreated check was 73.2 cm
*Butyl 2-[(5-chloro-8-quinolyl)oxy]acetimidate
**Butyl 2-[(5-chloro-8-quinolyl)oxy]acetate

EXAMPLE 10

Evaluation of a foliar application of 2,4-D on the synergistic interaction between two pesticides The procedure used is the same as described in Example 3, except that the plants are sprayed with 2,4-dichlorophenoxyacetic acid (2,4-D) as the amine formulation and the herbicide primisulfuron in sufficient quantities to provide 0–0.75 kg/ha of 2,4-D and 0.02–0.04 kg/ha of primisulfuron when applied to the plants with a 40 psi nozzle. The results are reported in Table X.

TABLE X

| Treatment | Rate (kg/ha) | % Growth Reduction |
|---|---|---|
| Untreated check | 0.00 | 0 |
| Terbufos | 1.00 | 3 |
| Primisulfuron | 0.02 | 6 |
| Terbufos × Primisulfuron | 1.0 × 0.02 | 34 |
| Terbufos × Primisulfuron + 2,4-D | 1.0 × 0.02 0.25 | 22 |
| Terbufos × Primisulfuron + 2,4-D | 1.0 × 0.02 0.50 | 13 |
| Terbufos × Primisulfuron + 2,4-D | 1.0 × 0.02 0.75 | 18 |
| Primisulfuron | 0.04 | 13 |
| Terbufos × Primisulfuron | 1.0 × 0.04 | 41 |
| Terbufos × Primisulfuron + 2,4-D | 1.0 × 0.04 0.25 | 55 |
| Terbufos × Primisulfuron + 2,4-D | 1.0 × 0.04 0.50 | 19 |
| Terbufos × Primisulfuron + 2,4-D | 1.0 × 0.04 0.75 | 30 |

Shoot height of the untreated check was 73.2 cm

EXAMPLE 11

Evaluation of a foliar application of dicamba on the synergistic interaction between two pesticides The procedure used is the same as described in Example 3, except that plants are sprayed with 2-methoxy-3,6-dichlorobenzoic acid (dicamba) and primisulfuron in sufficient quantities to provide 0–0.5 kg/ha of dicamba and 0.02–0.04 kg/ha of primisulfuron when applied to the plants with a 40 psi nozzle.

The results are reported in Table XI.

TABLE XI

| Treatment | Rate (kg/ha) | % Growth Reduction |
|---|---|---|
| Untreated check | 0.00 | 0 |
| Terbufos | 1.00 | 3 |
| Primisulfuron | 0.02 | 6 |
| Terbufos × Primisulfuron | 1.0 × 0.02 | 34 |
| Terbufos × Primisulfuron + Dicamba | 1.0 × 0.02 0.125 | 15 |
| Terbufos × Primisulfuron + Dicamba | 1.0 × 0.02 0.25 | 12 |
| Terbufos × Primisulfuron + Dicamba | 1.0 × 0.02 0.50 | 29 |
| Primisulfuron | 0.04 | 13 |
| Terbufos × Primisulfuron | 1.0 × 0.04 | 41 |
| Terbufos × Primisulfuron + Dicamba | 1.0 × 0.04 0.125 | 48 |

TABLE XI-continued

| Treatment | Rate (kg/ha) | % Growth Reduction |
|---|---|---|
| Terbufos × Primisulfuron + Dicamba | 1.0 × 0.04 0.25 | 55 |
| Terbufos × Primisulfuron + Dicamba | 1.0 × 0.04 0.50 | 41 |

Shoot height of the untreated check was 73.2 cm

EXAMPLE 12

Field evaluation of a foliar application of 2,4-D on the synergistic interaction between two pesticides Field trials are conducted in a randomized complete block design with three replications. Each plot measures 3.05×9.15 meters. The preemergence herbicides alachlor and atrazine are applied over the entire plot area at rates of 2.24 and 1.12 kg/ha, respectively. In treatments containing insecticide, terbufos is applied in-furrow at 1.0 kg/ha. The corn variety used in this experiment is LYNKS DS-432.

When the plants have reached the 2-leaf stage, they are sprayed with either the herbicide nicosulfuron as ACCENT® 75 DF (manufactured by DuPont Co) at 0.036 kg/ha or the herbicide primisulfuron at 0.04 kg/ha, alone or in combination with 0.28 kg/ha of 2,4-D. Applications of herbicide, with and without a safener compound, are made with a tractor-mounted sprayer delivering 224 l/ha.

Ratings are taken six, fourteen and twenty-nine days after postemergence treatments. Crop injury is evaluated as percent decrease in plant height and is based on visual observations, in which no injury is assigned a 0% rating, and maximum injury is assigned a 100% rating. Data obtained are averaged and shown in Table XII.

TABLE XII

| Treatment | Rate (kg/ha) | % Decrease in Plant Height | | |
|---|---|---|---|---|
| | | 6 DAT | 14 DAT | 29 DAT |
| Untreated check | 0.00 | 0 | 0 | 0 |
| Terbufos In-Furrow | 1.00 | 0 | 0 | 0 |
| Nicosulfuron | 0.036 | 0 | 0 | 0 |
| Terbufos × Nicosulfuron | 1.0 × 0.036 | 35 | 23 | 6 |
| Terbufos × Nicosulfuron + 2,4-D Amine | 1.0 × 0.036 0.28 | 3 | 0 | 2 |
| Primisulfuron | 0.040 | 3 | 0 | 0 |
| Terbufos × Primisulfuron | 1.0 × 0.040 | 15 | 50 | 27 |
| Terbufos × Primisulfuron + 2,4-D Amine | 1.0 × 0.040 0.28 | 6 | 18 | 5 |
| 2,4-D Amine | 0.28 | 0 | 0 | 0 |

Terbufos was applied as the 15% granular formulation, COUNTER® 15G soil insecticide.
Nicosulfuron was applied as the 75 DF formulation, ACCENT® herbicide.
Primisulfuron was applied as the 75 DF formulation, BEACON® herbicide.
2,4-D-Amine was applied as the 4 AS formulation.

EXAMPLE 13

Field evaluation of naphthalic anhydride applied directly to the insecticide on the synergistic interaction between two pesticides Field trials are conducted in two randomized complete block designs with three replications each. Each plot measures 3.05×9.15 meters. The preemergence herbicides alachlor and atrazine are applied over the entire plot area at rates of 2.24 and 1.12 kg/ha respectively. Terbufos as COUNTER® 15G is applied in-furrow treated and untreated with a 20-40% wettable powder formulation of naphthalic anhydride. The untreated terbufos is applied at a rate of 1.0 kg/ha. The treated terbufos is applied at a rate of 1.0 kg/ha of terbufos and 0.125-0.25 kg/ha of naphthalic anhydride. The procedure for treating the terbufos is the same as described in Example 2.

The corn varieties used are DOCKDORF 7670 in the first evaluation and PIONEER 3744 in the second. When the plants have reached the 2-leaf stage, they are sprayed with the herbicide primisulfuron at 0.04 kg/ha. Postemergence applications are made with a tractor-mounted sprayer delivering 224 l/ha.

Ratings are taken at intervals after postemergence treatments. Crop injury is based on visual observations in which no injury is assigned a 0% rating and maximum injury is assigned a 100% rating. Ratings obtained are averaged and shown in Table XIII.

TABLE XIII

| | | % Overall Crop Injury | | | | |
|---|---|---|---|---|---|---|
| | | Trial 1 | | | Trial 2 | |
| Treatment | Rate (kg/ha) | 14 DAT | 41 DAT | 61 DAT | 30 DAT | 45 DAT |
| Untreated Check | 0.00 | 0 | 0 | 0 | 0 | 0 |
| Terbufos In-Furrow | 1.00 | 0 | 4 | 2 | 0 | 0 |
| Primisulfuron | 0.040 | 0 | 2 | 2 | 0 | 0 |
| Terbufos × Primisulfuron | 1.0 × 0.040 | 33 | 40 | 35 | 22 | 18 |
| Terbufos × Primisulfuron + Naphthalic Anhydride | 1.0 × 0.040 0.125 | 0 | 7 | 5 | 15 | 12 |
| Terbufos × Primisulfuron + Naphthalic Anhydride | 1.0 × 0.040 0.25 | 10 | 8 | 8 | 7 | 12 |

EXAMPLE 14

Field evaluation of naphthalic anhydride applied to the crop seed on the synergistic interactions between two pesticides Field trial procedures are repeated as described in Example 13, except that naphthalic anhydride is applied to the corn seed prior to planting at 0.25% w/w. The seeds are coated as described in Example 1.

The results are shown in Table XIV.

TABLE XIV

| Treatment | Rate (kg/ha) | % Overall Crop Injury | | | | |
|---|---|---|---|---|---|---|
| | | Trial 1 | | | Trial 2 | |
| | | 14 DAT | 41 DAT | 61 DAT | 30 DAT | 45 Dat |
| Untreated Check | 0.00 | 0 | 0 | 0 | 0 | 0 |
| Terbufos In-Furrow | 1.00 | 0 | 4 | 2 | 0 | 0 |
| Primisulfuron | 0.040 | 0 | 2 | 2 | 0 | 0 |
| Terbufos × Primisulfuron | 1.0 × 0.040 | 33 | 40 | 35 | 22 | 18 |
| Terbufos × Primisulfuron + Naphthalic Anhydride | 1.0 × 0.040 0.25% seed wt | 17 | 10 | 8 | 0 | 0 |
| Naphthalic Anhydride | 0.25% seed wt | 7 | 3 | 3 | 5 | 2 |

Terbufos was applied as the 15% granular formulation, COUNTER ® 15G.
Primisulfuron was applied as the 75 DF formulation, BEACON ®.

EXAMPLE 15

Evaluation of naphthalic anhydride applied as a seed treatment on the synergistic interaction between an organophosphate insecticide and a preemergence application of an imidazolinone herbicide Corn seeds (Pioneer 3475) are treated with naphthalic anhydride (formulated as a 20% wettable powder) by coating with safener at 0.05 grams per 100 grams seed (equal to 0.05% by seed weight).

Experiments are conducted in sterilized soil. Soil is placed in 10-inch×10-inch×2-inch shallow plastic flats, and thoroughly moistened. Two six-inch furrows are made in each flat, into each are placed five corn seeds, either coated or uncoated with the safener. In one series of flats, the organophosphate insecticide terbufos is applied to one furrow as the 15% granular formulation (COUNTER ® 15G) at a rate equivalent to 1 kg/ha; the other furrow is left untreated. In another series of flats, the organophosphate insecticide phorate is applied to one furrow as the 20% granular formulation (THIMET ® 20G) at a rate equivalent to 1 kg/ha; the other furrow is left untreated. The flats are sprayed preemergence with a commercial formulation of the herbicide imazethapyr containing 240 mg/mL active ingredient (PURSUIT ® 2AS manufactured by American Cyanamid Co.) The herbicide is diluted with water to provide the equivalent of 0.025 and 0.05 kg/ha when applied through a spray nozzle operating at 40 psi for a predetermined time.

After spraying, the flats are placed on greenhouse benches, watered and cared for in accordance with conventional greenhouse procedures.

From 2-4 weeks after treatment, the tests are terminated and each flat is examined and rated by measuring the height of the foliage.

The test results are averaged and expressed as a percent growth reduction compared to an untreated check, as described in Example 1. The data obtained are shown in Table XV.

TABLE XV

| Treatment | Rate (kg/ha) | % Growth Reduction |
|---|---|---|
| Untreated check | 0.0 | 0 |
| Terbufos | 1.0 | 0* |
| Phorate | 1.0 | 0** |
| Imazethapyr | 0.025 | 24 |
| Terbufos × Imazethapyr | 1.0 × 0.025 | 72 |
| Terbufos × Imazethapyr + Naphthalic Anhydride | 1.0 × 0.025 0.05% w/w | 34 |
| Phorate × Imazethapyr | 1.0 × 0.025 | 48 |
| Phorate × Imazethapyr + Naphthalic Anhydride | 1.0 × 0.025 0.05% w/w | 28 |
| Imazethapyr + Naphthalic Anhydride | 0.025 0.05% w/w | 2 |
| Imazethapyr | 0.05 | 42 |
| Terbufos × Imazethapyr | 1.0 × 0.05 | 85 |
| Terbufos × Imazethapyr + Naphthalic Anhydride | 1.0 × 0.05 0.05% w/w | 41 |
| Phorate × Imazethapyr | 1.0 × 0.05 | 86 |
| Phorate × Imazethapyr + Naphthalic Anhydride | 1.0 × 0.05 0.05% w/w | 35 |
| Imazethapyr + Naphthalic Anhydride | 0.05 0.05% w/w | 22 |

Shoot height of the untreated check was 64.2 cm
*Growth was 12% greater than the untreated check.
**Growth was 2% greater than the untreated check.

EXAMPLE 16

Evaluation of naphthalic anhydride applied as a seed treatment on the synergistic interaction between an organophosphate insecticide and a postemergence application of an imidazolinone herbicide Corn seeds (Pioneer 3475) are treated with naphthalic anhydride (formulated as a 20% wettable powder) by coating with safener at 0.05 grams per 100 grams seed (equal to 0.05% by seed weight).

Experiments are conducted in sterilized loamy sand soil containing 5% organic matter. Soil is placed in 10-inch×10-inch×2-inch shallow plastic flats, and thoroughly moistened. Two six-inch furrows are made in each flat, into each are placed five corn seeds, either coated or uncoated with the safener. The organophosphate insecticide terbufos is applied to one furrow as the 15% granular formulation (COUNTER ® 15G) at a rate equivalent to 1.0 kg/ha; the other furrow is left untreated.

Plants are sprayed at intervals ranging from the 2-leaf to the 7-leaf stage. A commercial formulation of the herbicide imazethapyr is diluted with water to provide the equivalent of 0.035 kg/ha of herbicide to the foliage when applied through a spray nozzle operating at 40 psi for a predetermined time. The herbicide spray solution contains 0.25% of the spray adjuvant CHARGER E, an alkylaryl polyethoxyethanol and N-butanol 80% non-ionic wetting agent manufactured by Blue Ribbon Products Co. Flats are then placed on greenhouse benches, watered and cared for in accordance with conventional greenhouse procedures.

From 2-4 weeks after treatment, the tests are terminated and each flat is examined and rated by measuring the height of the foliage. The test results are averaged and expressed as a percent growth reduction compared to an untreated check, as described in Example 1.

The results are shown in Table XVI.

TABLE XVI

| Treatment | Rate (kg/ha) | % Growth Reduction Growth Stage at Herbicide Application | | | |
|---|---|---|---|---|---|
| | | 2 Leaf | 3 Leaf | 5-6 Leaf | 6-7 Leaf |
| Untreated Check | 0.0 | 0 | 0 | 0 | 0 |
| Terbufos | 1.0 | 1 | 2 | 2 | 2 |
| Imazethapyr | 0.035 | 16 | 22 | 19 | 29 |
| Terbufos × Imazethapyr | 1.0 × 0.035 | 76 | 62 | 44 | 44 |
| Terbufos × Imazethapyr + Naphthalic Anhydride | 1.0 × 0.035 0.05% seed wt | 48 | 35 | 40 | 43 |
| Imazethapyr + Naphthalic Anhydride | 0.05% seed wt | 13 | 20 | 8 | 21 |

Shoot heights of untreated checks were: 64.4 cm (2L); 71.4 cm (3L); 88.4 cm (5-6L); 93.0 cm (6-7L)

EXAMPLE 17

Field evaluation of a foliar application of 2,4-D on the synergistic interaction between an organophosphate insecticide and a postemergence application of an imidazolinone herbicide Field trials are conducted as described in Example 12, except that the imidazolinone herbicide imazethapyr (applied as the formulated product PURSUIT ® 2AS), is applied postemergence to corn either alone, or in combination with 2,4-D.

The results are shown in Table XVII.

TABLE XVII

| Treatment | Rate (kg/ha) | % Decrease in Plant Height | | |
|---|---|---|---|---|
| | | 6 DAT | 4 DAT | 9 DAT |
| Untreated check | 0.00 | 0 | 0 | 0 |
| Terbufos In-Furrow | 1.00 | 0 | 0 | 0 |
| Imazethapyr | 0.036 | 45 | 24 | 15 |
| Terbufos × Imazethapyr | 1.0 × 0.036 | 52 | 89 | 75 |
| Terbufos × Imazethapyr + 2,4-D Amine | 1.0 × 0.036 0.028 | 52 | 42 | 18 |
| Terbufos × Imazethapyr | 1.0 × 0.036 | 55 | 58 | 32 |
| Terbufos × Imazethapyr + 2,4-D Amine | 1.0 × 0.036 0.28 | 15 | 13 | 0 |
| Imazethapyr + 2,4-D Amine | 0.036 + 0.28 | 8 | 7 | 5 |

Terbufos was applied as the 15% granular formulation., COUNTER ® 15G.
Imazethapyr was applied as the 2 AS formulation of PURSUIT ®.
2,4-D-Amine was applied as the 4 AS formulation.

What is claimed is:

1. A method of protecting maize or corn from injury which comprises applying an effective amount of a safener compound 1-carbethoxyethyl-3,6-dichloro-2methoxybenzoate (1) to the plant seed at a rate of at least 0.2% seed weight or (2), to the plant at a rate of at least 0.125 kg/ha, wherein said safener reduces the phytotoxic synergistic interaction of a phosphorodithioate insecticide and an acetohydroxyacid synthase-inhibiting herbicide selected from the group consisting of sulfonylurea herbicides and imidazolinone herbicides, each of which is applied in conjunction with said safener compound.

2. The method according to claim 1 wherein the organophosphate insecticide is terbufos or phorate.

3. The method according to claim 1 wherein the acetohydroxyacid synthase-inhibiting herbicide is primisulfuron.

4. The method according to claim 1 wherein the safener compound is applied to the corn plant seed.

5. The method according to claim 1 wherein the safener compound is applied to the corn plant.

6. The method according to claim 2 wherein the organophosphate insecticide is terbufos.

7. A composition to protect maize or corn from injury which comprises an acetohydroxyacid synthase-inhibiting herbicide selected from the group consisting of sulfonylurea herbicides and imidazolinone herbicides, in an amount which is phytotoxic in the presence of a phosphorodithioate insecticide, and a safener compound 1-carbethoxyethyl-3,6-dichloro-2-methoxybenzoate in an amount effective to reduce the phytotoxic synergistic interaction of said phosphorodithioate insecticide and said acetohydroxyacid synthase-inhibiting herbicide.

8. The composition according to claim 7 wherein the herbicide is primisulfuron.

* * * * *